United States Patent
Spindler et al.

(10) Patent No.: US 10,434,291 B2
(45) Date of Patent: Oct. 8, 2019

(54) CURVED PASSAGEWAY CONFORMING BALLOON CATHETER WITH NESTED BALLOONS

(71) Applicant: Cook Medical Technologies LLC, Bloomington, IN (US)

(72) Inventors: Ralf Spindler, Bloomington, IN (US); James Merk, Terre Haute, IN (US); Brent Mayle, Spencer, IN (US); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 211 days.

(21) Appl. No.: 15/707,340

(22) Filed: Sep. 18, 2017

(65) Prior Publication Data

US 2018/0147394 A1     May 31, 2018

Related U.S. Application Data

(60) Provisional application No. 62/426,782, filed on Nov. 28, 2016.

(51) Int. Cl.
    *A61M 25/10*     (2013.01)
    *A61F 2/958*     (2013.01)
    *A61B 17/22*     (2006.01)

(52) U.S. Cl.
    CPC .......... *A61M 25/1002* (2013.01); *A61F 2/958* (2013.01); *A61M 25/104* (2013.01);
(Continued)

(58) Field of Classification Search
    CPC .......... A61B 2017/22051; A61F 2/958; A61F 2002/9583; A61M 25/1002;
(Continued)

(56) References Cited

U.S. PATENT DOCUMENTS

| 4,744,366 A | 5/1988 | Jang |
| 5,147,377 A | 9/1992 | Sahota |

(Continued)

FOREIGN PATENT DOCUMENTS

| EP | 0835673 | 4/1998 |
| EP | 2082776 | 7/2009 |

OTHER PUBLICATIONS

European Patent Office, European Search Report for Application No. 17203355.7, dated Apr. 18, 2018, Munich Germany.

*Primary Examiner* — Jocelin C Tanner
(74) *Attorney, Agent, or Firm* — Liell & McNeil

(57) ABSTRACT

A balloon catheter includes a first balloon positioned inside of a second balloon, both of which are mounted about a catheter and fluidly connected to respective inflation lumens. In a first inflated configuration, the second balloon is inflated and has a shape that includes a plurality of bulb segments, with each two consecutive bulb segments being separated by a waist hoop. In a second inflated configuration both the inner and outer balloons are inflated, and the inner balloon bears radially outwardly against the waist hoop of the outer balloon such that the waist hoop of the outer balloon has a larger diameter in the second inflated configuration than in the first inflated configuration. The bulb segment separated by waist hoops enable the balloon catheter to conform to curved passageways, such as during the implementation of a stent.

20 Claims, 2 Drawing Sheets

(52) U.S. Cl.
CPC ............... *A61B 2017/22051* (2013.01); *A61F 2002/9583* (2013.01); *A61M 25/1011* (2013.01); *A61M 2025/1013* (2013.01); *A61M 2025/1061* (2013.01)

(58) Field of Classification Search
CPC ............ A61M 25/1011; A61M 25/104; A61M 2025/1013; A61M 2025/1061
See application file for complete search history.

(56) References Cited

U.S. PATENT DOCUMENTS

| | | | |
|---|---|---|---|
| 5,320,605 | A | 6/1994 | Sahota |
| 5,352,199 | A * | 10/1994 | Tower ............... A61M 25/1002 604/103.07 |
| 5,725,535 | A | 3/1998 | Hegde et al. |
| 5,788,708 | A | 8/1998 | Hegde et al. |
| 6,022,359 | A | 2/2000 | Frantzen |
| 6,471,672 | B1 | 10/2002 | Brown et al. |
| 6,527,739 | B1 | 3/2003 | Bigus et al. |
| 6,761,734 | B2 | 7/2004 | Suhr |
| 6,776,771 | B2 | 8/2004 | van Moorlegem et al. |
| 7,004,963 | B2 | 2/2006 | Wang et al. |
| 2012/0209375 | A1 * | 8/2012 | Madrid ................. A61F 2/2433 623/2.11 |
| 2012/0283636 | A1 | 11/2012 | Rizq et al. |
| 2013/0030519 | A1 | 1/2013 | Tran et al. |
| 2014/0135891 | A1 | 5/2014 | Poehlmann et al. |
| 2015/0367112 | A1 | 12/2015 | Gelbart |

* cited by examiner

US 10,434,291 B2

CURVED PASSAGEWAY CONFORMING BALLOON CATHETER WITH NESTED BALLOONS

TECHNICAL FIELD

The present disclosure relates generally to balloon catheters, and more particularly to a nested balloon strategy that better permits the inflated balloon to conform to the curvature of a passageway.

BACKGROUND

Most balloon catheters have a balloon that assumes a regular cylindrical shape when inflated. Although balloon catheters generally have the ability to bend, most balloon catheters may undesirably tend to cause a straightening of a passageway when the balloon is inflated. This issue can become more problematic when a balloon catheter is being used to expand a stent in a curved passageway. Instead of the stent conforming to the curvature of the passageway, the balloon catheter and stent can tend to cause a straightening of the passageway with the resultant more acute passageway curvatures occurring at the opposite ends of the implanted stent. Because these scenarios can tend to alter the smooth curvature of a passageway even if properly stented, undesirable results can occur. For instance, the likelihood of restenosis may be increased.

The present disclosure is directed to one or more of the problems set forth above.

SUMMARY

In one aspect, a balloon catheter includes a first balloon mounted about a catheter and fluidly connected to a first inflation lumen. A second balloon is mounted about the catheter and fluidly connected to a second inflation lumen. The first balloon is positioned inside the second balloon. The balloon catheter has a deflated configuration, a first inflated configuration and a second inflated configuration. The first inflated configuration is characterized by the second balloon being inflated and having a shape that includes a plurality of bulb segments. Each two consecutive bulb segments is separated by a waist hoop. Each of the bulb segments has a diameter greater than a diameter of the waist hoop. The second inflated configuration is characterized by the second balloon being inflated and the first balloon being inflated. The first balloon bears radially outward on the waist hoop such that the waist hoop has a larger diameter in the second inflated configuration than in the first inflated configuration.

In another aspect, the balloon catheter becomes a stent delivery system by having a stent mounted about the second balloon.

In still another aspect, a method of operating the balloon catheter includes positioning the balloon catheter at a site in a curved passageway. A centerline of the catheter conforms to match a curvature of the passageway by inflating the second balloon, and bending the catheter about a waist hoop of the second balloon, which is positioned between a pair of bulb segments. The waist hoops are then expanded by inflating the first balloon while the centerline of the catheter continues to match the curvature of the passageway.

DETAILED DESCRIPTION

Figure 1:
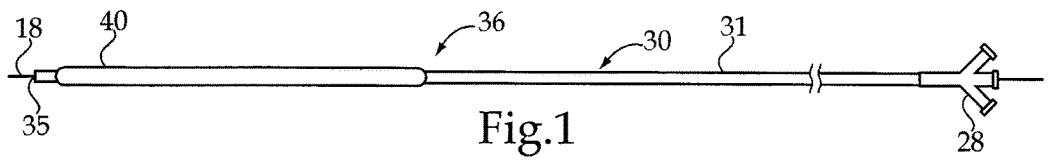
FIG. 1 is a side schematic view of a balloon catheter according to the present disclosure in a deflated configuration.
Figure 2:
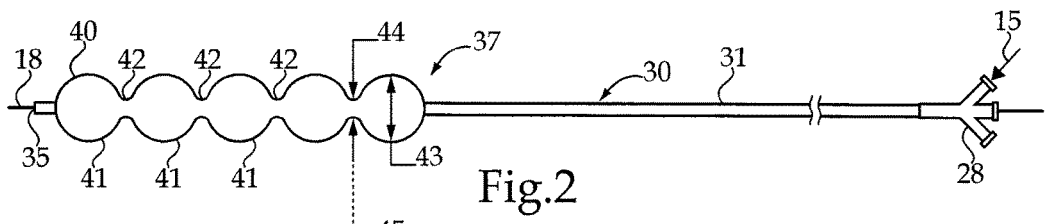
FIG. 2 is a side schematic view of the balloon catheter of FIG. 1 in a first inflated configuration.
Figure 3:
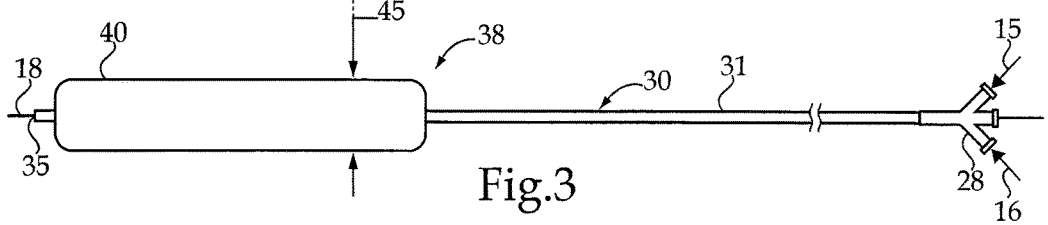
FIG. 3 is a side schematic view of the balloon catheter of FIG. 1 in a second inflated configuration.

Referring initially to FIGS. 1-7, a balloon catheter 30 according to the present disclosure includes a catheter 31 that defines a first inflation lumen 32 and a second inflation lumen 33. Catheter 31 may also define a wire guide lumen 34 that slidably receives a wire guide 18 in a conventional manner. An inner balloon 50 is mounted about the catheter 31 and fluidly connected to the first inflation lumen 32, such as through one or more ports 58. Inner balloon 50, maybe made from any suitable medical grade balloon material and attached to underlying catheter 31 in a conventional manner. A second or outer balloon 40 is also mounted about catheter 31 and fluidly connected to the second inflation lumen 33, such as via one or more ports 48. Like inner balloon 50, outer balloon 40 may be made from conventional medical grade balloon materials and attached to catheter 31 using conventional techniques and strategies. The inner balloon 50 is positioned inside the outer balloon 40. FIGS. 1, 2 and 3 show balloon catheter 30 in a deflated configuration 36, a first inflated configuration 37 and a second inflated configuration 38, respectively. Likewise, the enlarged sectioned views of FIGS. 4, 5 and 6 also show the deflated configuration 36, the first inflated configuration 37 and the second inflated configuration 38, respectively. Catheter 31 may include a fitting 28 attached at its proximal end to facilitate access to the respective lumens 32, 33 and 34. For instance, the center port of fitting 28 may be positioned to slidably receive a wire guide 18 that may extend distally beyond the distal end 35 of catheter 31 through wire guide lumen 34 that opens through distal end 35 of catheter 31. Catheter 31 may be manufactured from any suitable medical grade materials known in the art.

When balloon catheter 30 is in a deflated configuration 36, it may be maneuvered through a passageway within a body to arrive at a treatment site. After arriving at a treatment site, the balloon catheter may be changed from the deflated configuration 36 to the first inflated configuration 37 by inflating outer balloon 40 with a first inflation source 15, such as a syringe with a suitable balloon inflation fluid such as saline solution. When the outer balloon 40 is inflated, it assumes a shape that includes a plurality of bulb segments 41. Each two consecutive bulb segments 41 is separated by a waist hoop 42. Each of the bulb segments 41 has a diameter 43 that is greater than a diameter 44 of the waist hoop 42. When in a curved passageway, the interaction of the bulb segments 41 with the walls of the passageway can tend to cause balloon catheter 30 to conform to the curvature of the passageway by bending about axes that intersect the respective waist hoops 42. The inner balloon 50 may remain deflated in the first inflated configuration 37. The outer balloon 40 may be manufactured to contain any number of bulb segments from two or more. In the illustrated embodiment, the outer balloon 40 includes five bulb segments, but there is no particular significance to this number. Outer balloon 40 may be manufactured to assume the alternating bulb segment 41, waist hoop 42 shape by making a wall thickness 46 of the balloon 40 thicker at waist hoop 42 than a wall thickness 47 at the center of bulb segments 41. With this structure, the balloon material at waist hoops 42 can be made less elastic than the balloon at bulb segments 41. Those skilled in the art will appreciate that other strategies may be utilized to make the bulb segments 41 more responsive to expansion by the inflation fluid than the waist hoops 42, including but not limited to the use of different wall thicknesses, different materials, and maybe even by added waist constraints at waist hoops 42 without departing from the scope of the present disclosure.

Figure 4:
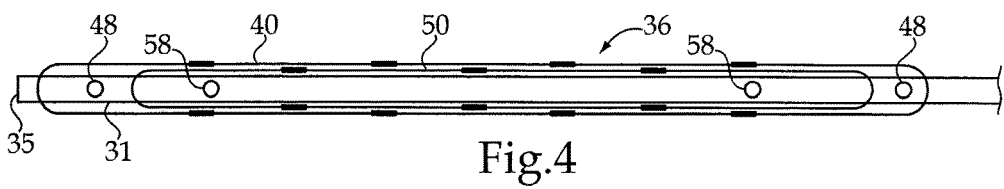
FIG. 4 is a sectioned side schematic view of the balloon portion of the balloon catheter of FIG. 1 in a deflated configuration.
Figure 5:
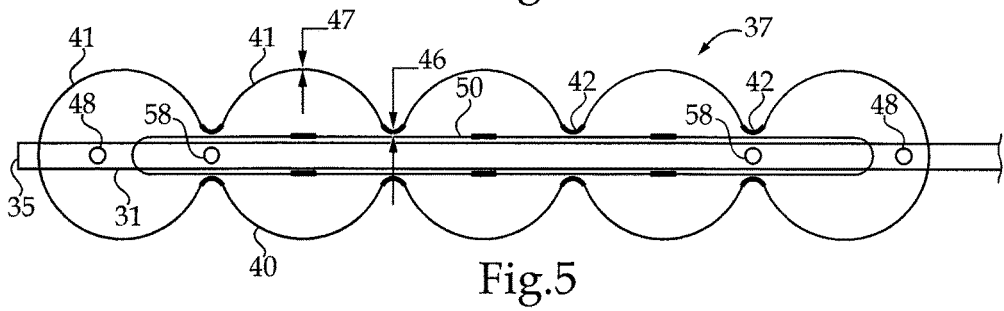
FIG. 5 is a sectioned view through the balloon in the first inflated configuration.
Figure 6:
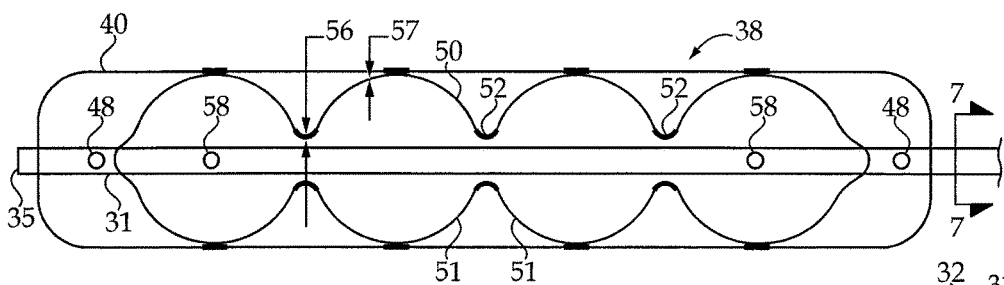
FIG. 6 is a side sectioned schematic view of the balloons in the second inflated configuration.
Figure 7:
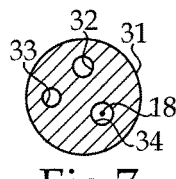
FIG. 7 is a sectioned view through the catheter as viewed along section lines 7-7 of FIG. 6.
Figure 8:
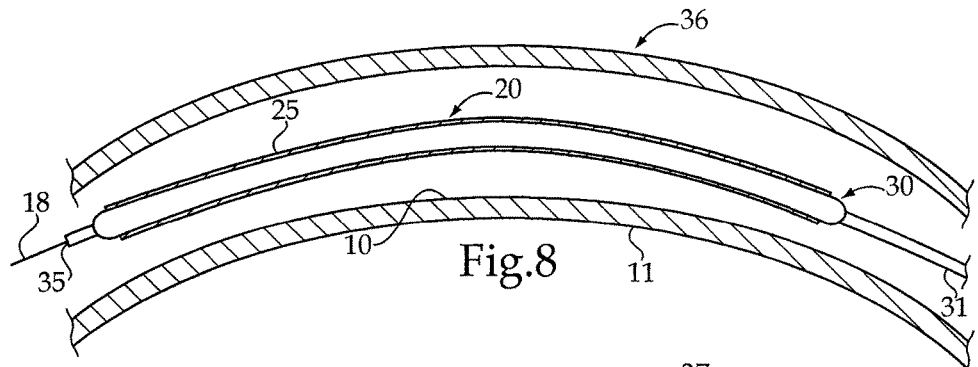
FIG. 8 is a side schematic view of a stent delivery system according to the present disclosure positioned at a site in a curved passageway.

One may transition from the first inflated configuration 37 to the second inflated configuration 38 by inflating the inner balloon 50. Thus, the second inflated configuration 38 may be characterized by the outer balloon 40 being inflated and the inner balloon 50 also being inflated. The inner balloon 50 is configured to bear radially outward against the waist hoops 42 as best shown in FIG. 6 such that the waist hoops 42 have a larger diameter 45 in the second configuration 38 than the diameter 44 in the first inflated configuration 37. The inner balloon 50 may be inflated with a second inflation source 16 that may be coupled to fitting 28 in a conventional manner. In most instances, the inner balloon 50 will be shorter than the outer balloon 40 along a longitudinal axis of catheter 31 as shown in FIGS. 4-6. Inner balloon 50 may have a structure similar to outer balloon 40 in that it may include a plurality of bulb segments 51, with each two consecutive bulb segments 51 being separated by a waist hoop 52. Inner balloon 50 may include a similar structure in that it may have a wall thickness 56 at waist hoops 52 that is thicker than the wall thickness 57 of the balloon material at the center of bulb segments 51. Thus, in the second inflated configuration 38, the outer balloon 40 may have an appearance similar to conventional inflated balloons that have a somewhat regular cylindrical shape. Those skilled in the art will appreciate that a variety of structural strategies may be utilized to cause the inner balloon 50 to bear against and expand the waist hoops 42 of the outer balloon 40. These include varying wall thicknesses as described, and may include and is not limited to the use of alternative materials, or make the additional waist hoop material constraints that cause the inner balloon 50 to assume the shape shown in, for instance in FIG. 6. Or, inner balloon 50 may be attached to catheter 31 at waist hoops 52, but still allow for the passage of inflation fluid between adjacent bulb segments 51. In those instances where both the inner balloon 50 and the outer balloon 40 tend to include the alternating bulb segments waist hoop configurations shown, the waist hoops 52 may be out of phase with the waist hoops 42 of the outer balloon 40. This example structure assumes that the length between respective bulb segments 52, 42 is about the same for the outer balloon 40 and inner balloon 50. Nevertheless, those skilled in the art will appreciate that other strategies could be utilized without departing from the scope of the present disclosure.

In the illustrated embodiment, the diameter of the waist hoops 52 of the inner balloon 50 are smaller than the diameters of respective bulb segments 52 of the inner balloon 50. Preferably, the outer balloon 40 will have a plurality of waist hoops 42 and at least three bulb segments 41 in the first inflated configuration 37. Each of the waist hoops 42 will have a larger diameter 45 in the second inflated configuration 38 than the diameter 44 in the first inflated configuration 37. Although not necessary, the outer surface of inner balloon 50 may be out of contact with the inner surface of waist hoops 42 of the outer balloon in the first inflated configuration 37, as best shown in FIG. 5. Nevertheless, structures in which the outer surface of the inner balloon 50 are always in contact with the inner surface of outer balloon 40 are also contemplated. In fact, the inner balloon 50 may actually be attached to the various locations, such as at the waist hoops 42 of the outer balloon 40 without departing from the intended scope of the present disclosure. In the specific embodiment shown, the diameter of waist hoops 42 in the second inflated configuration 38 may be about equal to the diameter 43 of the bulb segments 41 in the first inflated configuration 37. As used in this disclosure, the term about equal means that the ratio of the two diameters, when rounded to a single significant digit, is one. For example, 1.3 is about equal to 0.9; however, 1.6 is not about equal to 1.0. Assuming a construction similar to that shown in FIGS. 1-7, the bulb segments 41 of the outer balloon 40 may be out of phase with the bulb segments 51 of the inner balloon 50.

Although balloon catheter 30 may be utilized as an expansion device, such as for angioplasty in the vascular system, balloon catheter 30 may become a stent delivery system 20 (FIGS. 8-11) when a stent 25 is mounted about the outer balloon 40 in a conventional manner. This strategy may help promote implantation of stent 25 in a curved passageway such that the step inflation of the balloon catheter from the first inflation configuration to the second inflation configuration can cause the stent to conform to match the curvature of the passageway in which the stent is implanted.

INDUSTRIAL APPLICABILITY

The present disclosure find potential application in any medical balloon catheter. Although the present disclosure may finds specific applicability for usage in vascular passageways, the present disclosure is not so limited and could be utilized with appropriate scaling in other body passageways, including but not limited to the gastrointestinal tract or elsewhere. The present disclosure finds specific applicability as either an angioplasty balloon catheter or a stent delivery system that better conforms to the curvature of a curved passageway at a delivery site rather than tending to straighten the passageway as in the prior art.

Figure 9:
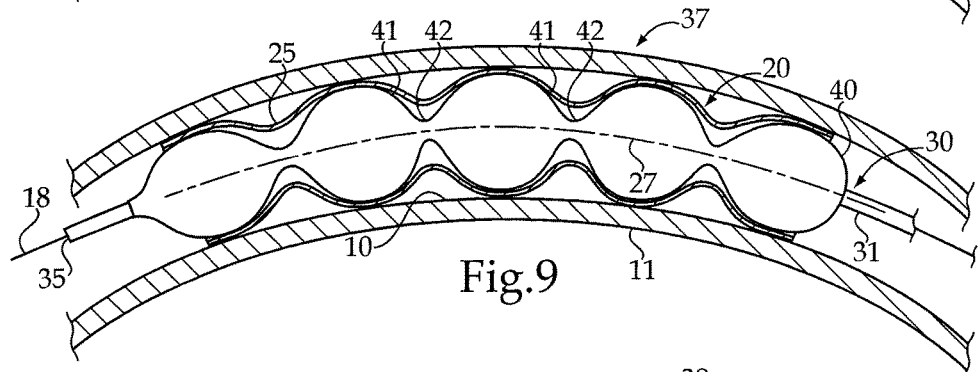
FIG. 9 is a side schematic view of the stent delivery system of FIG. 8 in the first inflated configuration.
Figure 10:
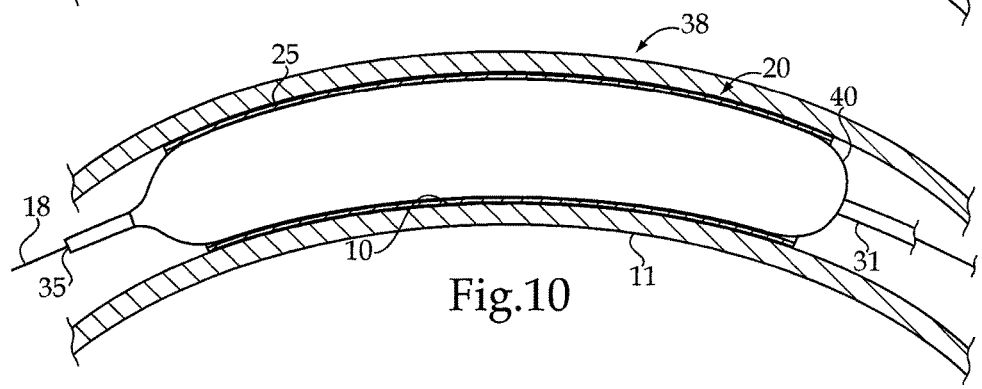
FIG. 10 is a side schematic view of the stent delivery system in the second inflated configuration.
Figure 11:
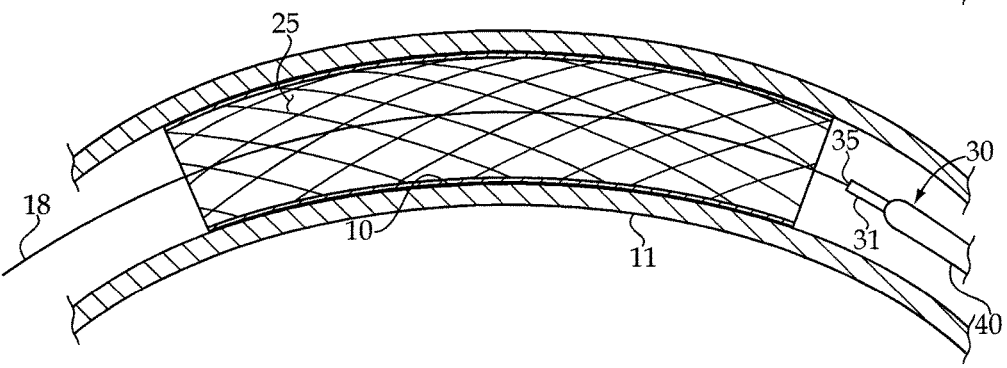
FIG. 11 is a side schematic view showing the balloon catheter in a deflated configuration being moved away from the implanted stent in the curved passageway.

Referring now in addition to FIGS. 8-11, a method of operating stent delivery system 20 and hence balloon catheter 30 is illustrated. First a wire guide 18 may be positioned past a site 10 in a curved passageway 11. Thereafter, the stent delivery system 20, in the deflated configuration 36, may be slid along wire guide 18 until arriving at site 10 in curved passageway 11. A centerline 27 of catheter 31 may be conformed to match the curvature of passageway 11 by transitioning to the first inflated configuration 37 by inflating the outer balloon 40. Conforming to the curvature occurs by an interaction of the bulb segments 41 with the wall of the passageway 11 to cause the catheter 31 to bend about waist hoops 42, as best shown in FIG. 9. It should be noted that FIG. 9 shows that the stent 25 is only partially expanded and also tends to bend to match the curvature of passageway 11. Thereafter, the waist hoops 42 may be expanded from their first smaller diameter 44 (FIG. 2) to a larger diameter 45 (FIG. 3) as shown in FIG. 10 by transitioning to the second inflated configuration 38. After stent 25 is fully expanded as shown in FIG. 10, the balloon catheter 30 may be returned to its deflated configuration 36 and moved away and out of contact with stent 25 as best shown in FIG. 11 to complete the implantation. Thus, the stent 25 is expanded in two steps so that it may first conform to the curvature of the passageway 11 as shown in FIG. 9, and then have its expansion completed by inflating the inner balloon 50 to expand the areas associated with the waist hoops 42. Thus, the stent expands responsive to the inflation of the outer balloon 40 and then the inner balloon 50.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A balloon catheter comprising:
a catheter that defines a first inflation lumen and a second inflation lumen;
a first balloon mounted about the catheter and fluidly connected to the first inflation lumen;
a second balloon mounted about the catheter and fluidly connected to the second inflation lumen;
wherein the first balloon is positioned inside the second balloon;
the balloon catheter having a deflated configuration, a first inflated configuration and a second inflated configuration;
the first inflated configuration being characterized by the second balloon being inflated and having a shape that includes a plurality of bulb segments, and each two consecutive bulb segments being separated by a waist hoop, and each of the bulb segments having a diameter greater than a diameter of the waist hoop; and
the second inflated configuration being characterized by the second balloon being inflated and the first balloon being inflated, and the first balloon bearing radially outward on the waist hoop such that the waist hoop has a larger diameter in the second inflated configuration than in the first inflated configuration.

2. The balloon catheter of claim 1 wherein the second balloon has a plurality of waist hoops and at least three bulb segments in the first inflated configuration; and
each of the waist hoops has a larger diameter in the second inflated configuration than in the first inflated configuration.

3. The balloon catheter of claim 1 wherein a wall thickness of the second balloon is thicker at the waist hoop than at a center of the bulb segments.

4. The balloon catheter of claim 1 wherein the first balloon is out of contact with the waist hoop in the first inflated configuration.

5. The balloon catheter of claim 1 wherein the first balloon is deflated in the first inflated configuration.

6. The balloon catheter of claim 1 wherein a diameter of the waist hoop in the second inflated configuration is about equal to the diameter of the bulb segments in the first inflated configuration.

7. The balloon catheter of claim 1 wherein the first balloon includes a plurality of bulb segments, and each two consecutive bulb segments being separated by a waist hoop.

8. The balloon catheter of claim 1 the second balloon has a plurality of waist hoops and at least three bulb segments in the first inflated configuration;
the first balloon includes at least two bulb segments and at least one waist hoop; and
the bulb segments of the second balloon are out of phase with the bulb segments of the first balloon.

9. The balloon catheter of claim 1 wherein the catheter includes a wire guide lumen that opens through a distal end of the catheter.

10. A stent delivery system comprising:
a balloon catheter that includes a catheter that defines a first inflation lumen and a second inflation lumen, and a first balloon mounted about the catheter and fluidly connected to the first inflation lumen, and a second balloon mounted about the catheter and fluidly connected to the second inflation lumen, and the first balloon is positioned inside the second balloon;
a stent mounted about the second balloon;
the balloon catheter having a deflated configuration, a first inflated configuration and a second inflated configuration;
the first inflated configuration being characterized by the second balloon being inflated and having a shape that includes a plurality of bulb segments, and each two consecutive bulb segments being separated by a waist hoop, and each of the bulb segments having a diameter greater than a diameter of the waist hoop; and
the second inflated configuration being characterized by the second balloon being inflated and the first balloon being inflated, and the first balloon bearing radially outward on the waist hoop such that the waist hoop has a larger diameter in the second inflated configuration than in the first inflated configuration.

11. The stent delivery system of claim 10 wherein the second balloon has a plurality of waist hoops and at least three bulb segments in the first inflated configuration;
the first balloon includes at least two bulb segments and at least one waist hoop; and
the bulb segments of the second balloon are out of phase with the bulb segments of the first balloon.

12. The stent delivery system of claim 11 wherein a diameter of the waist hoop in the second inflated configuration is about equal to the diameter of the bulb segments in the first inflated configuration.

13. The stent delivery system of claim 12 wherein a wall thickness of the second balloon is thicker at the waist hoop than at a center of the bulb segments.

14. The stent delivery system of claim 10 wherein the catheter includes a wire guide lumen that opens through a distal end of the catheter; and
a wire guide slidably received in the wire guide lumen and extending distally beyond a distal end of the balloon catheter.

15. A method of operating a balloon catheter that includes a catheter that defines a first inflation lumen and a second inflation lumen, and a first balloon mounted about the catheter and fluidly connected to the first inflation lumen, and a second balloon mounted about the catheter and fluidly connected to the second inflation lumen, and the first balloon is positioned inside the second balloon, the method comprising the steps of:

positioning the balloon catheter at a site in a curved passageway;

conforming a centerline of the catheter to match a curvature of the passageway by inflating the second balloon, and bending the catheter about a waist hoop of the second balloon, which is positioned between a pair of bulb segments; and expanding the waist hoop by inflating the first balloon while the centerline of the catheter continues to match the curvature of the passageway.

16. The method of claim 15 wherein the second balloon has a plurality of waist hoops and at least three bulb segments in the first inflated configuration;

the first balloon includes at least two bulb segments and at least one waist hoop; and the bulb segments of the second balloon are out of phase with the bulb segments of the first balloon.

17. The method of claim 16 including a step of expanding a stent in the passageway responsive to the steps of inflating the second balloon and inflating the first balloon; and the stent is expanded to a shape that conforms to the curvature of the passageway.

18. The method of claim 17 including deflating the first balloon and the second balloon; and moving the balloon catheter out of contact with the stent.

19. The method of claim 18 wherein the positioning step includes sliding the balloon catheter along a wire guide received in a wire guide lumen of the catheter.

20. The method of claim 19 wherein a wall thickness of the second balloon is thicker at the waist hoop than at a center of the bulb segments.

* * * * *